United States Patent [19]

Wenzel et al.

[11] Patent Number: 4,836,213
[45] Date of Patent: Jun. 6, 1989

[54] PRESSURE CONTROL SYSTEM FOR CONTINUOUS BLOOD PRESSURE MONITOR TRANSDUCER

[75] Inventors: Dennis J. Wenzel; Dean C. Winter; Kevin S. Honeyager, all of San Antonio, Tex.

[73] Assignee: Nippon Colin Co., Ltd., Komaki, Japan

[21] Appl. No.: 160,134

[22] Filed: Feb. 25, 1988

[51] Int. Cl.[4] .................................................. A61B 5/02
[52] U.S. Cl. ....................................... 128/672; 128/687
[58] Field of Search ................................. 128/672–690

[56] References Cited

U.S. PATENT DOCUMENTS

| | | | |
|---|---|---|---|
| 3,123,068 | 3/1964 | Bigliano | 128/672 |
| 3,219,035 | 11/1965 | Pressman | 128/672 |
| 3,880,145 | 4/1975 | Blick | 128/672 |
| 4,030,484 | 6/1977 | Kuska et al. | 128/672 |
| 4,185,621 | 1/1980 | Morrow | 128/672 |
| 4,423,738 | 1/1984 | Newgard | 128/675 X |

*Primary Examiner*—Kyle L. Howell
*Assistant Examiner*—Angela D. Sykes
*Attorney, Agent, or Firm*—Matthews & Branscomb

[57] ABSTRACT

A method for computing optimal hold down pressure for a transducer comprising an array of pressure sensing elements for generation of electrical waveforms indicative of blood pressure in an artery. Using the selected pressure sensing element that is determined to be positioned substantially over the center of the underlying artery, a set of data corresponding to the diastolic pressure and the pulse amplitude pressure is collected and stored. The diastolic pressures and pulse amplitude pressures are taken as a function of hold down pressure over a range of hold down pressures between the pressure at which the artery is unflattened and the pressure at which the artery is occluded. First and second polynomials are fitted to the diastolic pressure data set and the pulse amplitude data set, respectively. The hold-down pressure at the point of minimum slope of the first polynomial fitted to the diastolic versus hold-down pressures values provides one estimate of the correct hold-down pressure. Another estimate of the correct hold-down pressure using the pulse amplitude measurements is provided by locating the point where the slope of the second polynomial is zero. In another embodiment of the method of the present invention, the two above described estimates are combined into a single estimate.

5 Claims, 6 Drawing Sheets

PRESSURE CONTROL SYSTEM FOR CONTINUOUS BLOOD PRESSURE MONITOR TRANSDUCER

FIELD OF THE INVENTION

The present invention relates generally to a method an apparatus for continuous noninvasive measurement of blood pressure. More specifically, the present invention provides a method and apparatus for ascertaining the correct transducer hold-down pressure required for obtaining accurate blood pressure measurements.

BACKGROUND

There has been considerable interest in recent years in the development of a monitoring system for obtaining a continuous measurement of a patient's blood pressure. One of the most promising techniques for obtaining such a continuous measurement involves the use of an arterial tonometer comprising an array of small pressure sensing elements fabricated in a silicon "chip." The use of such an array of sensor elements for blood pressure measurements is disclosed generally in the following U.S. Patents: U.S. Pat. No. 3,123,068 to R. P. Bigliano, U.S. Pat. No. 3,219,035 to G. L. Pressman, P. M. Newgard and John J. Eige, U.S. Pat. No. 3,880,145 to E. F. Blick, U.S. Pat. No. 4,269,193 to Eckerle, and U.S. Pat. No. 4,423,738 to P. M. Newgard, and in an article by G. L. Pressman and P. M. Newgard entitled "A Transducer for the Continuous External Measurement of Arterial Blood Pressure" (IEEE Trans. Bio-Med. Elec., April 1963, pp. 73-81).

In a typical tonometric technique for monitoring blood pressure, a transducer which includes an array of pressure sensitive elements is positioned over a superficial artery, and a hold-down force is applied to the transducer so as to flatten the wall of the underlying artery without occluding the artery. The pressure sensitive elements in the array have at least one dimension smaller than the lumen of the underlying artery in which blood pressure is measured, and the transducer is positioned such that more than one of the individual pressure-sensitive elements is over at least a portion of the underlying artery. The output from one of the pressure sensitive elements is selected for monitoring blood pressure. The element that is substantially centered over the artery has a signal output that provides an accurate measure of intraarterial blood pressure. However, for the other transducer elements the signal outputs generally do not provide as accurate a measure of intraarterial blood pressure as the output from the centered element. Generally, the offset upon which systolic and diastolic pressures depend will not be measured accurately using transducer elements that are not centered over the artery. In some prior art arrangements the pressure sensitive element having the maximum pulse amplitude output is selected, and in other arrangements the element having a local minimum of diastolic or systolic pressure which element is within substantially one artery diameter of the element which generates the waveform of maximum pulse amplitude is selected.

The pressure measured by the selected pressure sensitive element, i.e., the element centered over the artery, will depend upon the hold-down pressure used to press the transducer against the skin of the subject. Although fairly accurate blood pressure measurements are obtained when a hold-down pressure within a rather wide pressure range is employed, it has been found that there exists a substantially unique value of hold-down pressure within said range for which tonometric measurements are most accurate. This so-called "correct" hold-down pressure varies among subjects. With prior art tonometric type transducers, the correct hold-down pressure often is not determined, thereby leading to inaccuracies in the blood pressure measurements. A method for determining optimal hold down pressure is disclosed in application Ser. No. 007,038 assigned to SRI International. The method disclosed in the present invention represents an improvement on the method disclosed in the aforementioned patent application.

SUMMARY OF THE INVENTION

The present invention includes a transducer array for generation of electrical waveforms indicative of blood pressure in an artery. Using the selected pressure sensing element that is determined to be positioned substantially over the center of the underlying artery, a set of data corresponding to the diastolic pressure and the pulse amplitude pressure is collected and stored. The diastolic pressures and pulse amplitude pressures are taken as a function of hold down pressure over a range of hold down pressures between the pressure at which the artery is unflattened and the pressure at which the artery is occluded. First and second polynomials are fitted to the diastolic pressure data set and the pulse amplitude data set, respectively. The hold-down pressure at the point of minimum slope of the first polynomial fitted to the diastolic versus hold-down pressures values provides one estimate of the correct hold-down pressure. Another estimate of the correct hold-down pressure using the pulse amplitude measurements is provided by locating the point where the slope of the second polynomial is zero. In another embodiment of the method of the present invention, the two above described estimates are combined into a single estimate.

DETAILED DESCRIPTION OF THE PREFERRED EMBODIMENT

Figure 1:
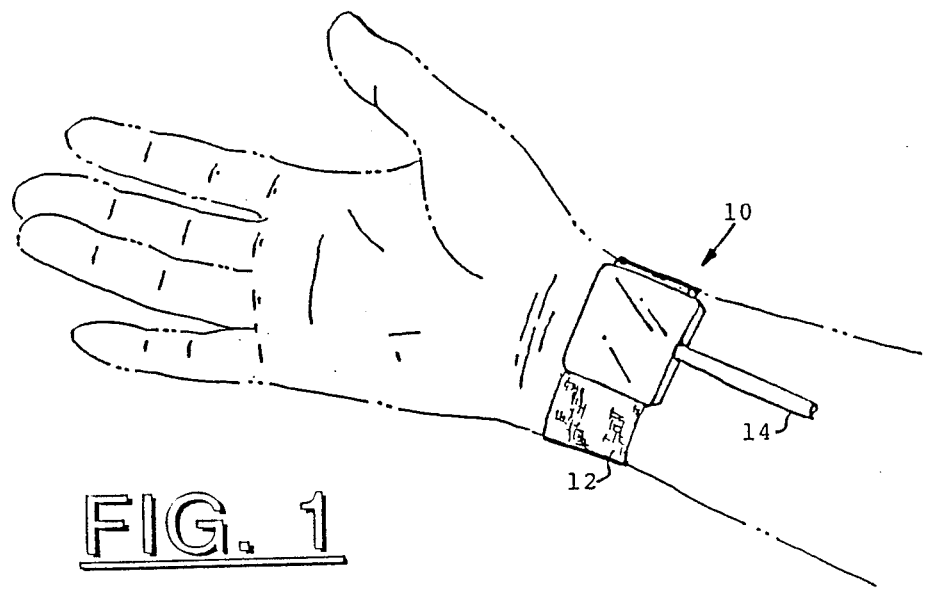
FIG. 1 is a view of the continuous blood pressure monitoring transducer of the present invention attached to a patient's wrist at a position overlying the radial artery.

Reference is now made to FIG. 1 wherein a continuous blood pressure monitor transducer 10 is shown attached to a patient's wrist at a point overlying the radial artery. The transducer is attached by means of a strap 12 in a manner similar to a conventional wristwatch. A cable assembly 14 connected to the transducer contains electrical cables for carrying electrical signals to and from the transducer. The cable assembly 12 also contains a pneumatic tube for providing pressurized air to a pressurizable bladder in the interior of the transducer in order to bring a sensor into contact with the patient's skin in a manner described in greater detail hereinbelow.

For the transducer to properly measure blood pressure it is important that the underlying artery be partially compressed. Specifically, it is important that the artery be flattened by a plane surface so that the stress developed in the arterial wall perpendicular to the face of the sensor are negligible. This generally requires that the blood pressure measurement be taken on a superficial artery which runs over bone, against which the artery can be flattened.

Figure 2:
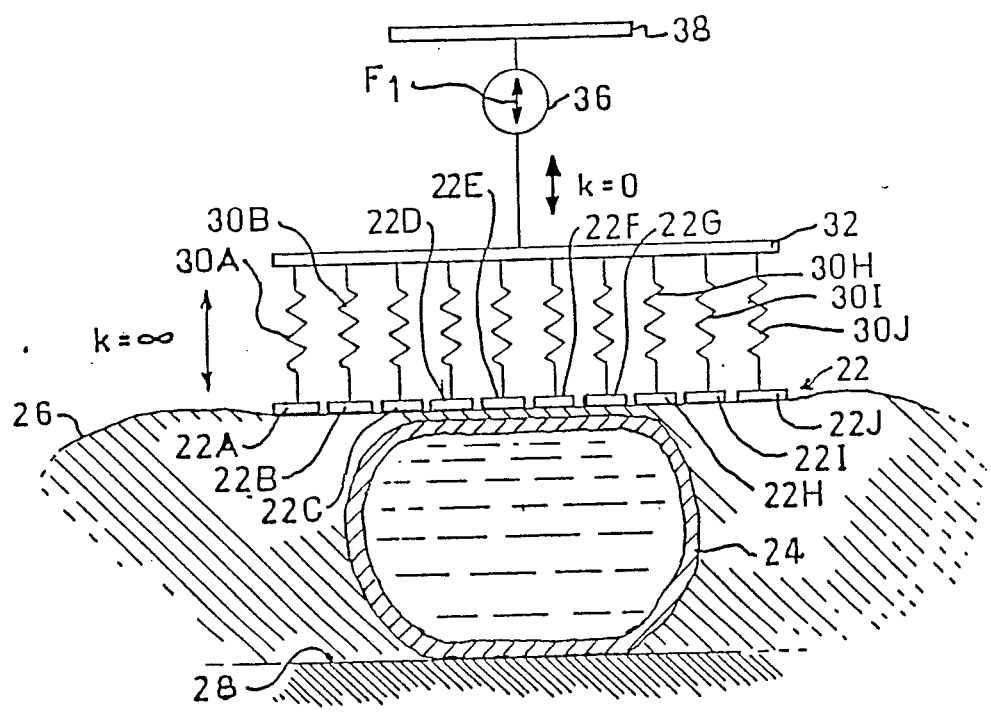
FIG. 2 is a schematic diagram illustrating the force balance between the artery and the multiple transducer elements (arterial riders), with the artery wall properly depressed to give accurate blood pressure readings.

Reference now is made to FIG. 2 wherein a diagrammatic mechanical model is shown which is representative of physical factors to be considered in blood pressure measurements using tonometry techniques. The illustrated models is adapted from that shown in the above-mentioned U.S. Pat. No. 4,269,193, issued to J. S. Eckerle, which by this reference is incorporated for all purposes. An array 22 of individual pressure sensitive elements or transducers 22-A through 22-E, which constitute the arterial riders, is positioned so that one or more of the riders are entirely over an artery 24. The individual riders 22-A through 22-E are small relative to the diameter of the artery 24, thus assuring that a plurality of the riders overlie the artery. The skin surface 26 and artery underlying the transducer must be flattened by application of a hold-down pressure to the transducer. One rider overlying the center of the artery is identified as the "centered" rider, from which rider pressure readings for monitoring blood pressure are obtained. Means for selecting the centered rider are discussed generally in the above mentioned U.S. Pat. No. 4,269,193. In addition, an improved means for selecting the best pressure sensing element for measuring blood pressure is disclosed in a patent application entitled "Active Element Selection for Continuous Blood Pressure Monitor Transducer" filed on even date herewith. For present purposes it will be understood that one of the riders, such as rider 22-E, may be selected as the "centered" rider, in which case the remainder of the riders, here riders 22-A through 22-D and 22-F through 22-J, comprise "side plates" which serve to flatten the underlying skin and artery.

Superficial arteries, such as the radial artery, are supported from below by bone which, in FIG. 2, is illustrated by ground symbol 28 under the artery. The wall of artery 24 behaves substantially like a membrane in that it transmits tension forces but not bending moments. The artery wall responds to the loading force of the transducer array, and during blood pressure measurements acts as if it is resting on the firm base 28. With the illustrated system, the transducer assembly 10 and mounting strap 12, together with air pressure applied to a pressurizable bladder in the transducer assembly, supply the required compression force and hold the riders 22-A through 22-J in such a manner that arterial pressure changes are transferred to the riders which overlie the artery 24. This is illustrated schematically in FIG. 2 by showing the individual riders 22-A through 22-J backed by rider spring members 30-A through 30-J, respectively, a rigid spring backing plate 32, and hold-down force generator 36 between the backing plate 32 and the mounting strap system 38.

If, without force generator 36, the coupling between the mounting strap system 38 and spring backing plate 32 were infinitely stiff to restrain the riders 22-A through 22-J rigidly with respect to the bone structure 28, the riders would be maintained in a fixed position relative to the artery. In practice, however, such a system is not practical, and hold-down force generator 36, comprising (in the present example) a pneumatic loading system, is included to keep constant the force applied by the mounting strap system 38 to riders 22-A through 22-J. In the mechanical model the spring constant, k (force per unit of deflection) of the force generator, 36, is nearly zero. Pneumatic loading systems are shown and described in the above-referenced U.S. Pat. Nos. 3,219,035 and 4,269,193, and the Pressman and Newgard IEEE article. In addition, an improved pneumatic loading system is disclosed in a patent application entitled "Pressurization System for Continuous Blood Pressure Monitor Transducer" filed on even date herewith.

In order to insure that the riders 22-A through 22-J flatten the artery and provide a true blood pressure measurement, they must be rigidly mounted to the backing plate 32. Hence, the rider springs 30-A through 30-J of the device ideally are infinitely rigid (spring constant $k = \alpha$). It is found that as long as the system operates in such a manner that it can be simulated by rider springs 30-A through 30-J having a spring constant on the order of about ten times the corresponding constant for the artery-skin system, so that the deflection of riders 22-A through 22-J is small, a true blood pressure measurement may be obtained when the correct hold-down pressure is employed.

Figure 3:
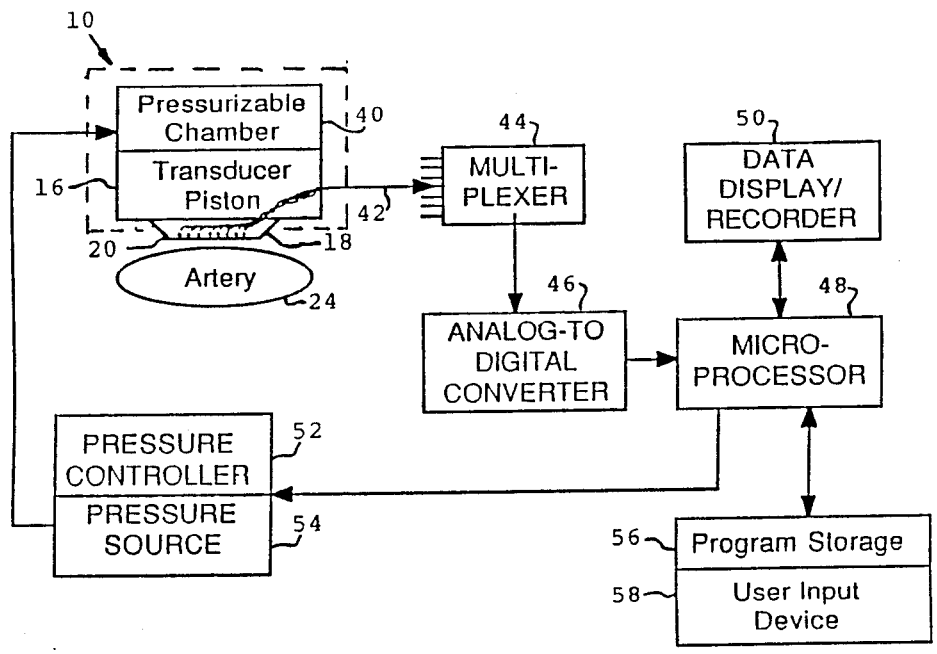
FIG. 3 is a simplified block diagram of the transducer assembly and associated system components for the continuous blood pressure monitoring system of the present invention.

Referring to FIG. 3, a simplified illustration of the transducer assembly 10 is shown to include a transducer piston 16, a pressurizable chamber 40 and a position controller 60. The output of the individual pressure sensors (not shown) on the sensor 20 are connected by appropriate electrical wiring 42 to the input of a multiplexer 44. From the multiplexer, the signals are digitized by an analog-to-digital (A-D) converter 46, and the digitized signals are supplied to a microprocessor 48. Output from the microprocessor 48 is supplied to data display and recorder means 50 which may include a recorder, cathode ray tube monitor, a solid state display, or any other suitable display device. Also, the output from the microprocessor is provided to the pressure controller 52 which controls a pressure source 54 to maintain the appropriate hold down pressure for the transducer piston 16. Operation of the microprocessor can be controlled by a program contained in program storage 56 or by user input from the user input device, which can be in the form of a keyboard or other interface device.

Figure 4:
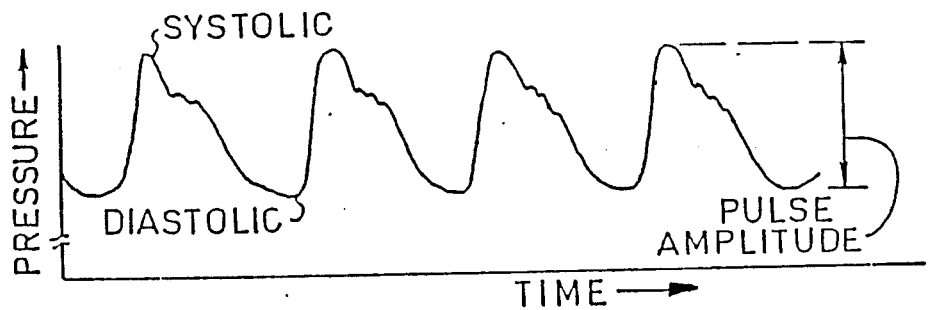
FIG. 4 is a waveform of human blood pressure versus time of the type which may be obtained using the present invention for illustrating systolic and diastolic pressures and pulse amplitude of the blood pressure wave.

Reference is now made to FIG. 4 which illustrates the signal waveform of the output from one of the pressure sensitive elements 22-A through 22-J which overlies artery 24. Other elements of the transducer array which overlie the artery will have waveforms of similar shape. With a correct hold-down pressure and correct selection of the "centered" arterial rider (i.e., the rider substantially centered over the artery) the waveform is representative of the blood pressure within the underlying artery. Systolic, diastolic and pulse amplitude pressures are indicated on the waveform, wherein pulse amplitude is the difference between the systolic and diastolic pressures for a given heartbeat.

Figure 5A:
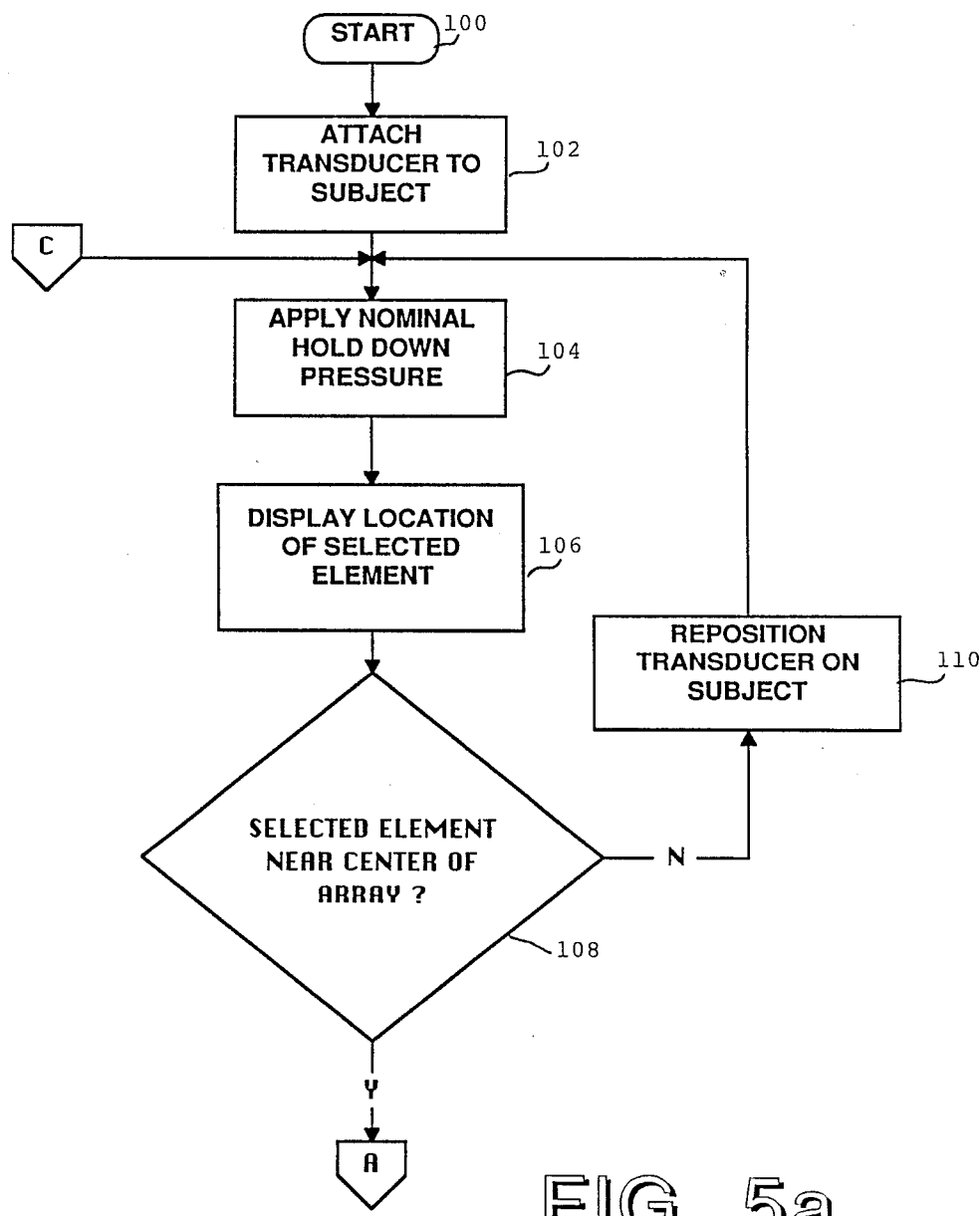
FIGS. 5A, 5B and 5C together show a flow chart for use in explaining overall operation of this invention.
Figure 5B:
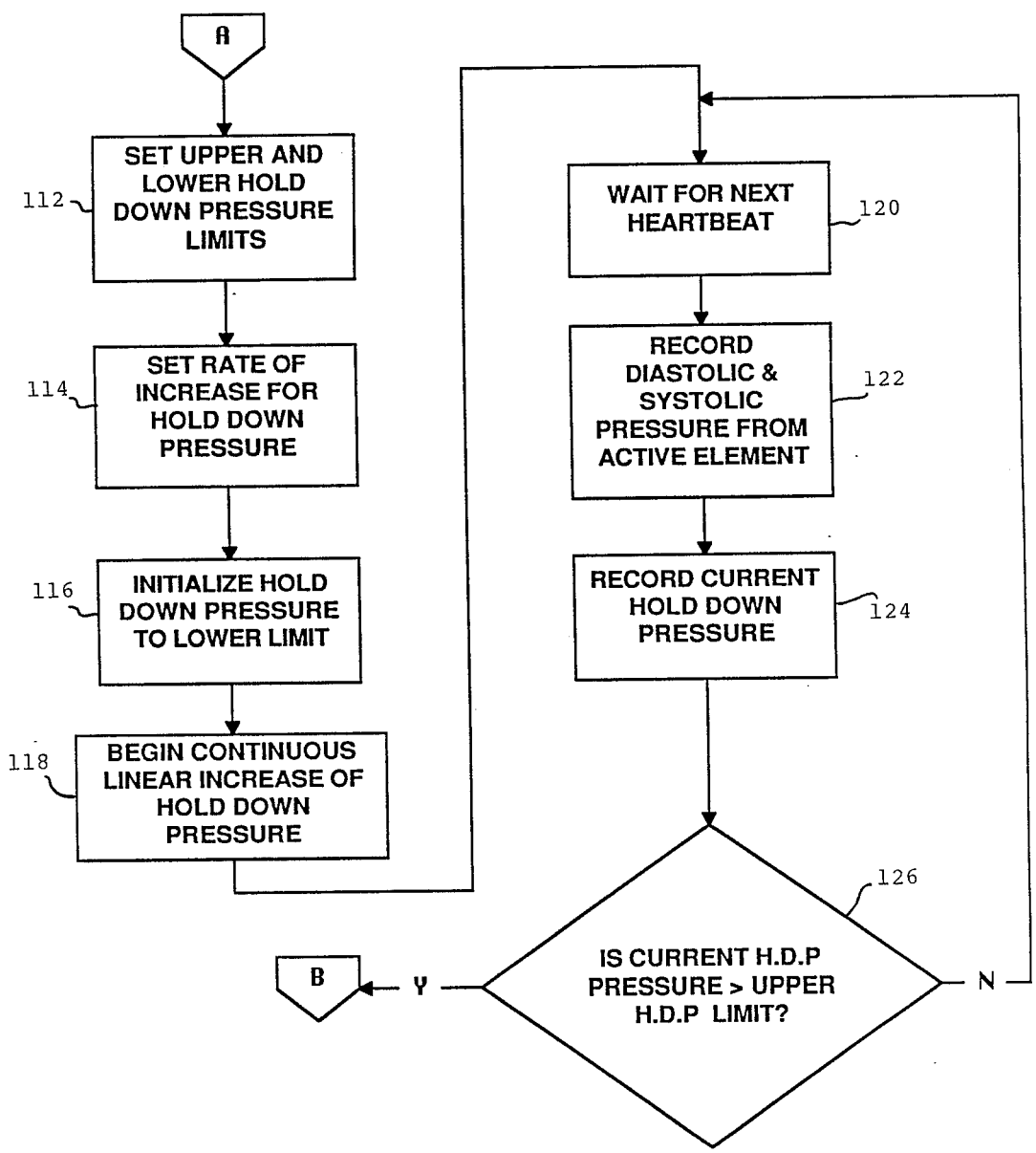
Figure 5C:
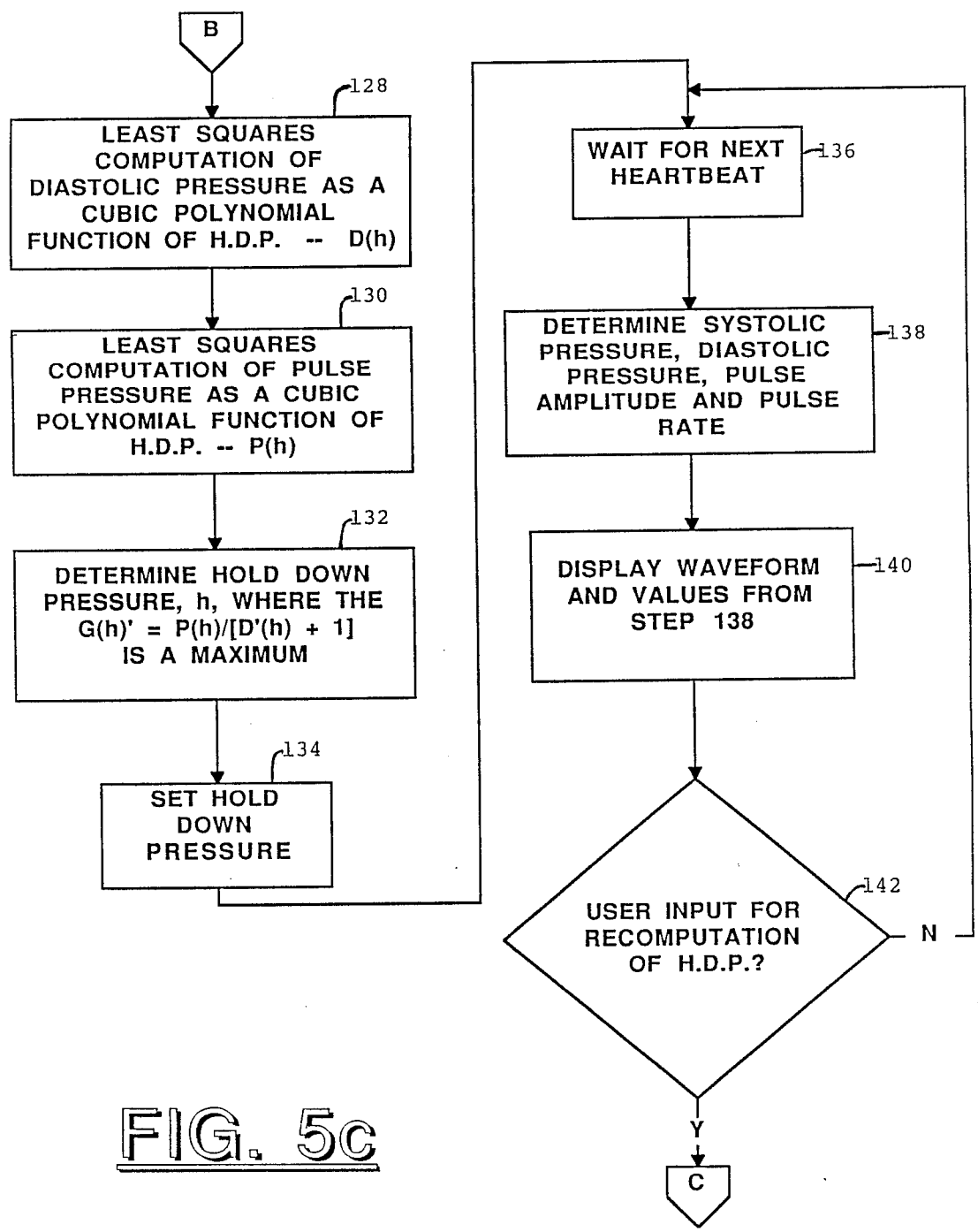

FIGS. 5A, 5B, and 5C together show a flow chart of an algorithm for general overall operation of the blood pressure monitoring system. Some of the operations indicated therein are under control of the microprocessor 48 responsive to programming instructions contained in program storage 56. Obviously, several program steps may be involved in the actual implementation of the indicated operations. Since the programming of such steps is well within the skill of the average programmer, a complete program listing is not required and is not included herein.

Preparation for monitoring is begun at START step 100, shown in FIG. 5A, at which time system power is turned on or a reset operation is performed by means not shown, and counters, registers, timers in the microprocessor 48 are initialized. Next, ate step 104, the transducer is attached to the patient at a location wherein a centrally located transducer element, such as element 22-E of tranducer array 22 overlies the center of the artery 24. Of course, the exact position of the transducer array relative to the subject, or operator, and repositioning of the transducer may be required to properly position the same. At step 104 a nominal hold down pressure (H.D.P.) is applied wherein air under pressure from source 54 is supplied to the transducer. For example, a hold-down pressure of 40 mmHg may be supplied to the transducer, which pressure serves to extend the pressurizable chamber 40 whereby the transducer piston extends outwardly a short distance from the bottom of the transducer case.

With the transducer attached to the subject, step 106 is entered and the location of the currently selected element is identified and displayed. At step 108, a decision is made about whether the currently selected element is in the center of the array of pressure sensing elements. If it is determined that the selected element is not near the center of the array, then step 110 is entered wherein the transducer is repositioned on the subject and step 106 is reentered. The process is repeated until the transducer is properly located on the subject. However, if the decision of step 108 is affirmative, then a series of data collection steps, shown in the flowchart of FIG. 5B, are entered beginning with step 112.

In step 112, upper and lower hold down pressure limits are set. These limits can be predetermined values stored in the memory of the computer 62, or can be entered by the operator. In step 114, the rate of increase is entered for varying the hold down pressure from the lower limit to the upper limit entered in step 112. Again, this value can be a predetermined value stored in the computer or can be a value entered by the operator. In step 116, the initial hold down pressure is initialized to the lower limit and in step 118 the hold down pressure is increased in a continuous linear manner until the detection of a heartbeat in step 120. Once a heartbeat has been detected, step 122 is entered wherein the systolic and diastolic pressures are recorded. Processes which may be employed in step 122, including identifying systolic and diastolic pressures, pulse amplitude, maxima, local minima, from the transducer outputs are readily implemented using the microprocessor 48. In step 124, the current hold down pressure is recorded and in step 126 the decision is made as to whether the current hold down pressure exceeds the upper hold down pressure limit. If hold down pressure does not exceed the upper limit, then step 120 is reentered. However, if it is determined that the upper limit has been exceeded, then a series of computational steps 128 through 134 is entered for the determination of optimal hold down pressure. Novel algorithms which may be used in computing the correct hold-down pressure will be described in greater detail below. For present purposes, it will be understood that a correct hold-down pressure for accurate blood pressure monitoring is computed and set at step 132, following which, at step 134, the computed hold-down pressure is set by control of pressure controller 52 by the microprocessor 48. With the transducer properly positioned on the subject and the correct hold-down pressure supplied thereto, the system is in condition for obtaining accurate blood pressure readings.

With the correct hold down pressure set, the step 136 is entered wherein the system waits for the next heartbeat. From the output of the selected transducer element, systolic and diastolic pressure values together with pulse amplitude values are readily determined in step 138. Also, pulse rate is readily calculated by determining the time between successive diastolic or systolic pressures. At step 140, values calculated and determined in step 138 are displayed and/or recorded along with the actual waveform.

After the values identified in step 122, such as systolic and/or diastolic pressure, are displayed, decision step 142 is entered wherein the system determines whether there has been a request from the operator for a recomputation of hold down pressure. If no such request has been received, step 136 is reentered wherein the system waits for the next heartbeat. However, if such a request for recomputation has been received, then the system returns to step 104, as shown in FIG. 5A.

DETERMINATION OF HOLD-DOWN PRESSURE

1. Diastolic Pressure vs. Hold-Down Pressure

Figure 6:
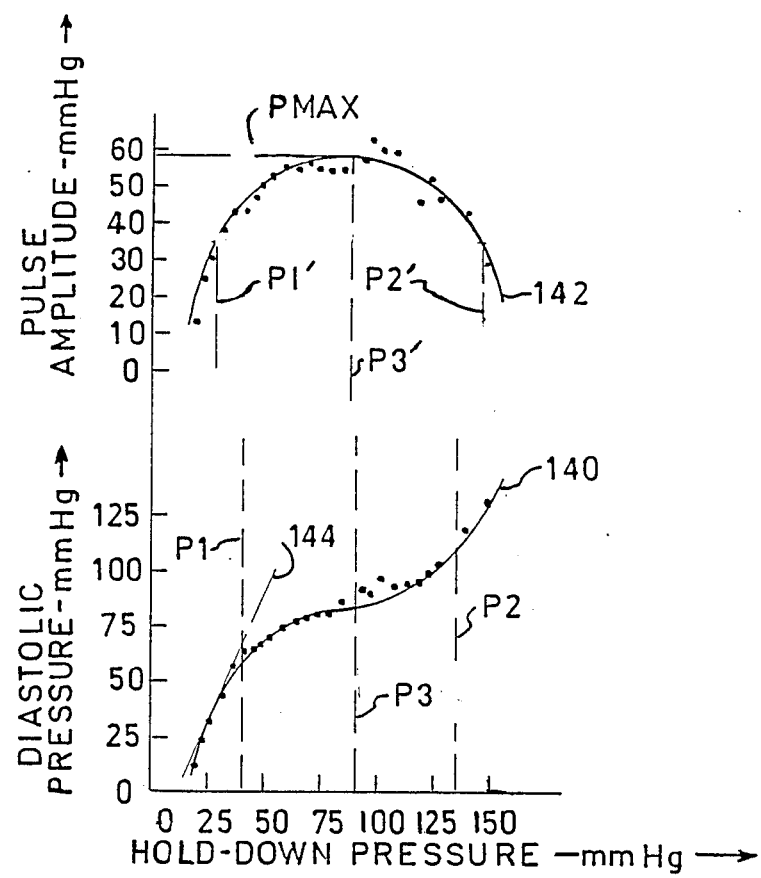
FIG. 6 shows plots of diastolic pressure and pulse amplitude versus hold-down pressure for a typical subject.

Reference now is made to FIG. 6 wherein plots of diastolic pressure and pulse amplitude versus hold-down pressure are shown which will facilitate an understanding of novel means for determining correct hold-down pressure for accurate blood pressure measurements. A third-order polynomial is fitted using, for example, least squares techniques to the FIG. 6 series of diastolic pressure points to provide a curve 140 which has the typical shape shown regardless of physical characterstics of the subject.

A third-order polynomial fitted to the measured data may be written as follows:

$$D(h) = a_0 + a_1 h + a_2 h^2 + a_3 h^3 \tag{1}$$

wherein:

$D(h)$ = measured diastolic pressure at hold down pressure h, h = hold-down pressure, and $a_0$, $a_1$, $a_2$, and $a_3$ are coefficients of the polynomial.

The derivative of the function $D(h)$ may be written as $D'(h) = a_1 + 2a_2 h + 3a_3 h^2$. This derivative will be used in the final selection of optimum hold down pressure, as discussed in greater detail below. For hold-down pressures between zero and P1, the underlying artery remains unflattened, and the measured pressure is primarily dependent upon the hold-down pressure and secondarily upon the intraarterial pressure, $P_a$. The graph of the polynomial is a relatively straight line over this range. Up to pressure P1, the effective spring constant of the artery, using the mechanical model of the system shown in FIG. 2, is large.

Between hold-down pressures P1 and P2, the hold-down pressure is great enough to partially flatten the underlying artery, but not great enough to occlude it. Experiments have shown that most accurate blood pressure measurements are obtained when a hold-down pressure that is substantially midway between pressures P1 and P2. Between pressures P1 and P2, the effective spring constant of the artery, using the mechanical model of FIG. 2, is relatively small.

At hold-down pressures greater than P2, the underlying artery is completely occluded, and the effective spring constant of the underlying artery is again relatively large. Consequently, the measured pressure is again substantially independent of the intraarterial pressure, $P_a$, and the curve is substantially a straight line above pressure P2. As seen in FIG. 6, the slope of curve 140 is lowest between pressures P1 and P2 where the underlying artery is flattened but not occluded. In theory, the correct hold down pressure could be determined from this curve alone by locating the minimum slope point, which is point P3 on FIG. 6.

2. Pulse Pressure vs. Hold Down Pressure

Reference is again made to FIG. 6 wherein plots of diastolic pressure and pulse amplitude versus hold-down pressure are shown. A third-order polynomial is again fitted using least squares techniques to the FIG. 6 series of pulse pressure points to provide a curve 142 which has the typical shape shown regardless of physical characteristics of the subject.

For the determination of the hold down pressure using the pulse amplitude points, it is highly desirable to use a mathematical relationship which provides a high correlation coefficient. It has been found that a third order polynomial provides this desired relationship. The third-layer polynomial fitted to the measured data may be written as follows:

$$P(h) = b_0 + b_1 h + b_2 h^2 + b_3 h^3 \quad (2)$$

wherein:

P(h) = measured pulse pressure at hold down pressure h, h = hold-down pressure, and $b_0$, $b_1$, $b_2$, and $b_3$ are coefficients of the polynomial.

In theory, the correct hold down pressure could be determined from this curve alone by locating the maximum point which is point P3' in FIG. 6. Furthermore, as discussed in greater detail below, it is expected that the maximum point P3' on curve 142 will coincide with the minimum slope point P3 for curve 140.

3. Combination Method

As discussed above, an optimum hold-down pressure can be estimated by finding the h value for which D(h) has a maximum slope in equation (1), or alternatively, by finding the h value for which P(h) is a maximum in equation (2). In order to best combine these two estimates, a new function G(h) is defined as follows:

$$G(h) = \frac{P(h)}{D'(h) + 1}$$

where D'(h) and P(h) are as defined hereinabove. The optimum hold-down pressure h is then computed to be that h for which G(h) is a maximum. This is best done by the microprocessor 48 sequentially computing G(h) for each discrete value of h while simultaneously searching for the maximum.

The basis for the method described above is related to the fact that G(h) will be maximum at some h if P(h) is maximum and D'(h) is minimum at h. At the minimum slope point of D(h), D'(h) is approximately zero. The term D'(h) + 1 was chosen to prevent a division by zero which could result in G(h) going to infinity. Such a result would have the effect of causing the D(h) curve to dominate the selection of hold down pressure. The method thus gives an estimate of the optimal hold-down pressure pulse amplitude and diastolic pressure methods described earlier when the latter two methods each produce the same result.

When the pulse amplitude and diastolic pressure methods differ, however, the present method produces an estimate of the optimum hold-down pressure which is a weighted average of the two different hold-down pressure estimates. For example, if there is a very small difference between the maximum and minimum value of the curve 142, then the function P(h) can be considered to be approximately a constat value, P. For this case:

$$G(h) = \frac{P}{D'(h) + 1}$$

The maximum of G(h) then occurs at the h for which D'(h) is a minimum. On the other hand, if the variation in the slope at the various points on the curve 140 is very small, then the function D'(h) can be considered to be a constant value D'. For this case:

$$G(h) = \frac{P(h)}{D' + 1}$$

The maximum G(h) occurs in this case at the same h for which P(h) is a maximum.

Although the method and apparatus of the present invention has been described in connection with the preferred embodiment, it is not intended to be limited to the specific form set forth herein, but on the contrary, it is intended to cover alternatives and equivalents as may reasonable be included within the spirit and scope of the invention as defined by the appended claims.

I claim:

1. A method for determining the optimum hold-down pressure for use in a blood pressure measuring system comprising steps of applying a minimum hold-down pressure to an external pressure transducer that includes a pressure sensitive element and obtaining a continuous measurement of pulse pressure in an underlying artery, obtaining a set of diastolic and systolic pressure measurements corresponding to a single hold-down pressure as the hold-down pressure is incremented;

computing a set of pulse amplitudes corresponding to each hold-down pressure by subtracting the corresponding diastolic from the corresponding systolic pressure;

fitting a first polynomial to the set of pulse amplitudes versus hold-down pressure, said polynomial describing the pulse amplitude as a function of the hold-down pressure designated herein as P(h);

fitting a second polynomial to the set of diastolic pressures versus hold-down pressures, said second polynomial describing the diastolic pressure as a function of the hold-down pressure and designated herein as D(h);

taking a first derivative with respect to the hold-down pressure of the polynomial D(h), designated herein as D'(h);

computing, for each discrete hold-down pressure, a function designated herein as G(h), wherein $$G(h) = \frac{P(h)}{D'(h) + 1}$$

selecting as the optimum hold-down pressure that pressure for which the computed G(h) is a maximum.

2. The method according to claim 1 wherein P(h) and D(h) are generated using a least squares calculation.

3. The method according to claim 2, wherein D(h) is a third order polynomial.

4. The method according to claim 3, wherein said P(h) is a third order polynomial.

5. The method according to claim 1, wherein a first derivative of G(h) is taken with respect to the hold-down pressure and the optimum hold-down pressure is selected as that for which said first derivative of G(h) is equal to zero.

* * * * *